(12) United States Patent
Davies et al.

(10) Patent No.: US 7,250,105 B1
(45) Date of Patent: *Jul. 31, 2007

(54) MEASUREMENT OF SUBSTANCES IN LIQUIDS

(75) Inventors: Oliver W. H. Davies, Inverness (GB); Christopher P. Leach, Inverness (GB); Manuel Alvarez-Icaza, Inverness (GB)

(73) Assignee: Lifescan Scotland Limited, Scotland (GB)

(*) Notice: Subject to any disclaimer, the term of this patent is extended or adjusted under 35 U.S.C. 154(b) by 369 days.

This patent is subject to a terminal disclaimer.

(21) Appl. No.: 10/431,140

(22) Filed: May 7, 2003

Related U.S. Application Data

(63) Continuation of application No. 09/521,163, filed on Mar. 8, 2000, now Pat. No. 6,733,655.

(51) Int. Cl.
*G01N 27/327* (2006.01)
*G01N 27/333* (2006.01)

(52) U.S. Cl. .................. 205/777.5; 205/789

(58) Field of Classification Search ............... 204/403.01–403.14, 416–418; 205/777.5, 205/778, 792
See application file for complete search history.

(56) References Cited

U.S. PATENT DOCUMENTS

| | | | |
|---|---|---|---|
| 5,004,998 A | 4/1991 | Horii | |
| 5,120,420 A * | 6/1992 | Nankai et al. | 204/403.11 |
| 5,234,813 A | 8/1993 | McGeehan et al. | |
| 5,582,697 A | 12/1996 | Ikeda et al. | |
| 5,628,890 A | 5/1997 | Carter et al. | |
| 5,650,062 A | 7/1997 | Ikeda et al. | |
| 5,672,256 A | 9/1997 | Yee | |
| 5,786,584 A | 7/1998 | Button et al. | |
| 5,791,344 A | 8/1998 | Schulman et al. | |
| 5,820,551 A | 10/1998 | Hill et al. | |
| 5,837,546 A | 11/1998 | Allen et al. | |
| 6,004,441 A * | 12/1999 | Fujiwara et al. | 204/403.14 |
| 6,287,451 B1 * | 9/2001 | Winarta et al. | 205/777.5 |
| 6,733,655 B1 * | 5/2004 | Davies et al. | 205/775 |

FOREIGN PATENT DOCUMENTS

| | | |
|---|---|---|
| EP | 0537761 A2 | 4/1993 |
| EP | 0942278 A2 | 9/1999 |
| WO | WO 97/02487 A1 | 1/1997 |
| WO | WO 9730344 A1 | 8/1997 |
| WO | WO 9958709 A1 | 11/1999 |

OTHER PUBLICATIONS

V.A. Bodner "Aviation Devices", The Machine Building Publishing House, Moscow, Russia, 1969, p. 158.
Official Action Issued by the Patent Office of the Russian Federation, mailed on or about Dec. 6, 2004, re Russuan Application No. 2002126814.

* cited by examiner

*Primary Examiner*—Alex Noguerola

(57) ABSTRACT

In accordance with the present invention a measuring device compares the current generated by two working sensor parts and gives an error indication if they are too dissimilar, i.e., the current at one sensor part differs too greatly from what would be expected from considering the current at the other. Not only can this method detect when one of the sensor parts has not been properly covered with sample liquid, but it can also detect if there is a manufacturing defect in either sensor part or if either has been damaged after manufacture, since even with complete coverage of the working sensor parts, an anomalous current will be generated at the affected sensor part under such circumstances.

3 Claims, 2 Drawing Sheets

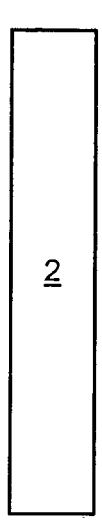
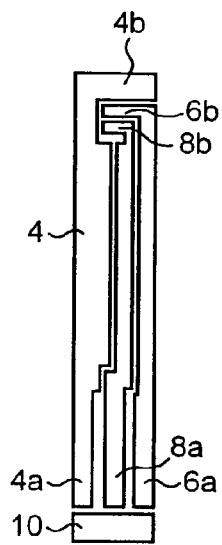
FIG. 1　　　　FIG. 2
FIG. 3　　　　FIG. 4
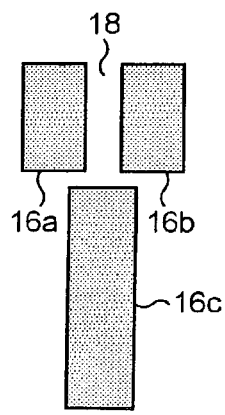
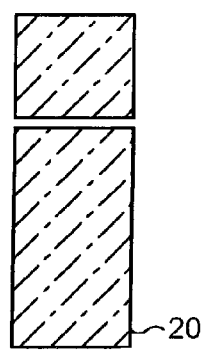
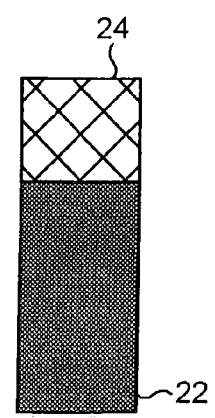
FIG. 5　　FIG. 6　　FIG. 7

MEASUREMENT OF SUBSTANCES IN LIQUIDS

This application is a Continuation application of Ser. No. 09/521,163 filed Mar. 8, 2000, now U.S. Pat. No. 6,733,655, which is incorporated herein by reference in its entirety.

This invention relates to apparatus for measuring the concentration of a substance in a liquid and particularly, but not exclusively, to apparatus for measuring the concentration of glucose in blood.

Devices for measuring blood glucose levels are invaluable for diabetics, especially devices that may be used by the sufferers themselves since they may then monitor their own glucose levels and take an appropriate dose of insulin. Correspondingly therefore the accuracy of such devices is very important since an inaccurate reading could lead to the wrong level of insulin being administered which could be very harmful.

It is also the case that in all practical blood glucose measuring systems at least part of the device, i.e. that part which comes into contact with the sample blood, is disposable. This means that it is particularly important that the cost particularly of any disposable parts can be minimised as a user will generally need large numbers of them regularly.

Known glucose measuring devices now favour an electrochemical measurement method over old colorimetric methods. The general principle is that an electric current is measured between two sensor parts called the working and reference sensor parts respectively. The working sensor part comprises a layer of enzyme reagent, the current being generated by the transfer of electrons from the enzyme substrate, via the enzyme and an electron mediator compound to the surface of a conductive electrode. The current generated is proportional to both the area of the sensor part and also the concentration of glucose in the test sample. Since the area of the working sensor part is supposedly known, the electric current should be proportional to the glucose concentration.

It has been recognised in the art that inaccurate results are obtained if the working sensor part is not fully covered with blood since then its effective area is reduced. Various ways of dealing with this problem have been proposed, two of which are disclosed in U.S. Pat. No. 5,628,890 and U.S. Pat. No. 5,582,697 Both of these methods rely on a unidirectional flow of blood across the surface of the test strip and both initiate the test measurement by detecting the presence of the sample liquid at an electrode or sensor part located downstream of the working sensor part.

The problem of insufficient sample liquid being present and thus the working sensor part not being completely covered may of course be reduced by reducing the size of the working sensor part. However a small area for the working sensor part tends to give a greater variability in calibrated results.

The present inventors have realised that as well as incomplete coverage of the working sensor part, inaccurate results can also arise from occasional defects in the production of the test strips for such devices, in the area and/or the thickness of the working sensor part and also from accidental damage to the working sensor part e.g by a user. As far as the inventors are aware, the only practical way to deal with this problem so far has been to ensure that the printing process used to produce the test strips is as accurate as possible and to rely on adequate quality control.

It is an object of the present invention at least partially to alleviate the above-mentioned disadvantages and when viewed from a first aspect the invention provides a method of measuring the concentration of a substance in a sample liquid comprising the steps of:

providing a measuring device having a first working sensor part comprising a working layer which generates an electric current proportional to the concentration of said substance in the sample liquid, a reference sensor part and a second working sensor part comprising a working layer which also generates an electric current proportional to the concentration of said substance in the sample liquid;

applying the sample liquid to said measuring device;

comparing the electric current generated at each of the working sensor parts to establish a difference parameter; and giving an indication of an error if said difference, parameter is greater than a predetermined threshold.

Furthermore the measuring device used in this method is novel and inventive in its own right and thus from a second aspect the present invention provides a device for measuring the concentration of a substance in a sample liquid, said device comprising:

a reference sensor part, a first working sensor part, comprising a working layer for generating an electric current proportional to the concentration of said substance in the sample liquid; and a second working sensor part comprising a working layer also for generating an electric current proportional to the concentration of said substance in the sample liquid.

Thus it will be seen that in accordance with the invention the measuring device compares the current generated by two working sensor parts and gives an error indication if they are too dissimilar—i.e. the current at one sensor part differs too greatly from what would be expected from considering the current at the other. Not only can this method detect when one of the sensor parts has not been properly covered with sample liquid, but it can also detect if there is a manufacturing defect in either sensor part or if either has been damaged after manufacture, since even with complete coverage of the working sensor parts, an anomalous current will be generated at the affected sensor part such circumstances.

In accordance with the invention the only type of defect or damage which would not necessarily be recognised is one which affected both of the working sensor parts to the same degree. However, this is logically less likely than a defect affecting a single working sensor part and is thus an improvement over the prior art. In practice such a likelihood is considered to be negligible. In any event the invention is not limited to providing just two working sensor parts and the skilled person could therefore choose to provide three or more working sensor parts to further reduce the probability that they are all affected by an identical defect.

Looking at the invention another way, it provides an arrangement whereby for a given total area of working sensor part and thus a given minimum sample volume, detection of inadequate fill and of defects in the working sensor part provided by separating the area of the working sensor part into two.

Some or all of the sensor parts may be provided as part of an integrated device. Preferably however at least the working sensor parts are provided on a removable test member. Thus when viewed from a further aspect the present invention provides a test member for measuring the concentration of a substance in a sample liquid comprising:

a substrate; and two working sensor parts provided on the substrate, each working sensor part comprising a working layer for generating an electric current proportional to the concentration of said substance in the sample liquid.

Preferably a reference sensor part is also provided on the substrate.

It will be appreciated by those skilled in the art that effectively what has been provided is a measuring device which is self-testing for proper use, damage and certain manufacturing defects. This is particularly beneficial in the context of a device in which the sensor parts are provided on a separate test member since this may typically be a mass-manufactured test strip, e.g. for measuring blood glucose levels. Since in accordance with the invention a damaged or defective test strip will be recognised, allowing it to be rejected, the accuracy of the final result and thus potentially the safety of a user is no longer solely dependent upon high manufacturing precision. Although it is of course not desirable that a large number of tests is rejected, in many circumstances it is more important that inaccurate results are not given.

The two working sensor parts may be dissimilar or different potentials may be applied to each sensor part in either of which cases the measuring device is preferably arranged to apply appropriate weights to the measurements returned by one or both working sensor parts to normalise them. The difference parameter could then for example be the simple arithmetic difference between the normalised current values. Preferably however the working layer of both sensor parts is of the same material and alternatively, but preferably additionally, both working sensor parts have the same area. Thus it is most preferred that the two working sensor parts are substantially identical. It is also preferred that the measuring device is arranged to apply the same potential to each sensor part. This allows the difference parameter to comprise a direct comparison between the respective currents at the sensor parts in order to determine whether a reliable measurement of the substance concentration can be made.

The two working sensor parts may be arranged as convenient within the device, or in accordance with the preferred embodiment, on the test member. The device or test member may be arranged to allow the sample liquid to flow freely over the working sensor parts. More preferably however the sample liquid is constrained to flow substantially unidirectionally across the working sensor parts.

It is presently preferred that the two working sensor parts are arranged one downstream of the other. This makes it possible to ensure that one of the sensor parts will always be completely covered before the other begins to be covered, thus avoiding the possibility, however small, that insufficient sample liquid is applied to cover both sensor parts and furthermore that each sensor part is partially covered by the same amount. It will be appreciated however that if the above-mentioned small risk is deemed acceptable, arrangements in accordance with the invention allow a much greater flexibility in the placement of the sensor parts than in known devices whilst still providing protection against an inadequate volume of sample liquid being used or other incorrect product usage or damage. It is also preferred that both working sensor parts are downstream of the reference sensor part.

The threshold used to determine an inaccurate measurement may be chosen as appropriate. Typically a threshold will be chosen empirically as a suitable value will depend on the inherent variability in the manufacturing process, the desired precision of results, etc. To some extent there is a trade-off between the accuracy which may be obtained by setting the threshold low and the proportion of measurements which are disregarded as being too inaccurate. Thus the threshold might advantageously be set at a level for example where no significant harm would be done to a patient relying on the results to administer insulin.

The difference parameter may be an absolute value—e.g. of the difference in currents measured at each sensor part, but is preferably dimensionless—e.g. a percentage of one or other of the measured currents.

The actual current value used to calculate the concentration of the substance may just be that from one of the working sensor parts, but is preferably a combination thereof, e.g. the sum or mean of the two. This gives the advantage that the maximum effective working area is utilised which further helps to increase the precision of the results obtained.

A particularly preferred embodiment of the invention is a device for measuring the concentration of glucose in blood, in which the two working sensor parts and the reference sensor part are provided on a disposable test strip.

A preferred embodiment of the invention will now be described, by way of example only, with reference to the accompanying drawings in which:

FIG. 1 shows a substrate for a test strip in accordance with the invention;

FIG. 2 shows the layout of carbon tracks applied to the substrate;

FIG. 3 shows the layer of insulation applied to the strip;

FIG. 4 shows the enzyme reagent layer;

FIG. 5 shows a layer of hydrophilic film;

FIG. 6 shows the cover layer of the strip;

FIG. 7 is a plot of the results obtained without using a method in accordance with the invention.

Figure 8:
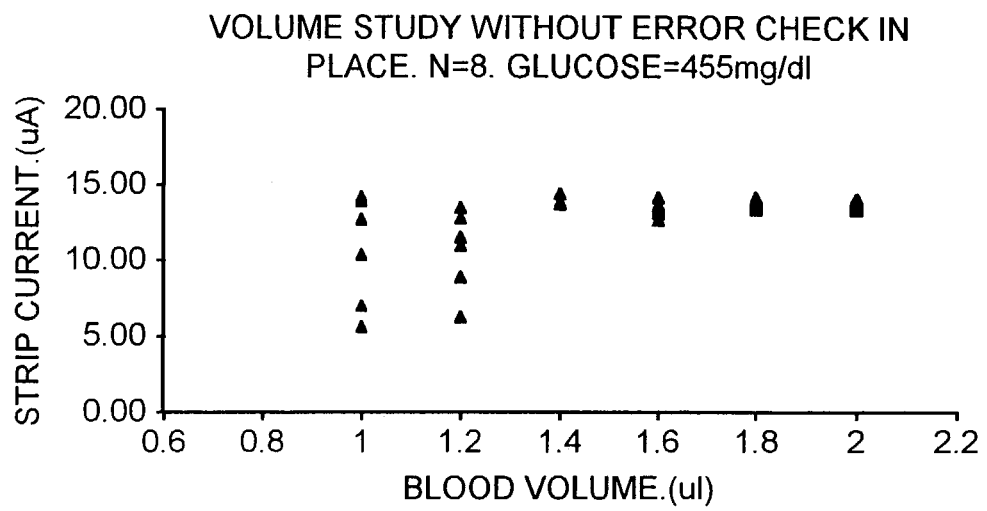
FIG. 8 is a plot similar to FIG. 7 obtained using a method in accordance with the invention.

Turning to FIG. 1, there is shown an oblong polyester strip 2 which forms the substrate for a test strip for measuring the concentration of glucose in a sample of blood. The substrate 2 is shown in isolation although in practice an array of such strips is cut out from a large master sheet at the end of fabrication.

FIG. 2 shows the pattern of carbon ink which is applied to the substrate by screen printing. The layer of carbon comprises four distinct areas which are electrically insulated from one another. The first track 4 forms, at the distal end thereof, an electrode 4b for a reference/counter sensor part. The track 4 extends lengthwise to form a connecting terminal 4a at its proximal end. The second and third tracks 6, 8 form electrodes 6b, 8b at their distal ends for two working sensor parts and respective connecting terminals 6a, 8a at their proximal ends. The fourth carbon area is simply a connecting bridge 10 which is provided in order to close a circuit in a suitable measuring device in order to turn it on when the test strip has been properly inserted.

FIG. 3 shows the next layer to be applied also by screen printing. This is a water insoluble insulating mask 12 which defines a window over the electrodes 6b, 8b and which therefore controls the size of the exposed carbon and hence where the enzyme layer 14 (FIG. 4) will come into contact with the carbon electrodes. The size and shape of the window are set so that the two electrodes 6b, 8b have a patch of enzyme of exactly the same area printed onto them. This means that for a given potential, each working sensor part will theoretically generate the same electric current in the presence of a sample of blood.

A layer of glucose oxidase 14 (FIG. 4) is printed over the mask 12 and thus onto the electrodes 4b, 6b, 8b through the window in the mask to form the reference/counter sensor part and the two working sensor parts respectively. A 150 micron layer of adhesive is then printed onto the strip in the pattern shown in FIG. 5. This pattern has been enlarged for clarity as compared to the previous Figures. Three separate areas of adhesive 16*a, b, c* together define a sample chamber 18 between them.

Two sections of hydrophilic film 20 (FIG. 6) are laminated onto the strip and are held in place by the adhesive 16. The first section of film has the effect of making the sample chamber 18 into a thin channel which draws liquid into and along it by a capillary action. The final layer is shown in FIG. 7 and is a protective plastic cover tape 22 which has a transparent portion 24 at the distal end. This enables a user to tell instantly if a strip has been used.

Use of the strip will now be described. The test strip is inserted into the meter. The bridge portion 10 completes a circuit in the device and thus automatically turns the device on. The device also has contacts to connect to the terminals 4*a*, 6*a*, 8*a* on the strip. The measuring device applies a potential of 400 mV between the counter/reference sensor part and each of the two working sensor parts via the above-mentioned terminals.

A drop of blood is then placed on the distal end of the strip. Capillary action draws the blood along the sample chamber 18 and over the counter/reference sensor part and two working sensor parts.

After a predetermined time the electric current generated by each working sensor part is measured and the two measurements are compared. If they differ by more than 10% an error message is displayed on the measuring device and the test must be repeated. If they are within 10% of each other however, the two currents are added together in the device and are converted to a glucose level which is displayed on an LCD.

A comparative experiment was carried out using a strip fabricated as set out above, in order to exemplify the benefits achievable in accordance with the invention. In the experiment drops of blood increasing in volume from 1 to 2 micro liters in steps of 0.2 micro liters and with a constant glucose concentration, were applied to such strips, with each volume being repeated 8 times. The current measured at each working sensor part was measured and recorded. The results are shown in Table 1 appended to this description.

For the first part of the test the two currents were simply added together to simulate a single working sensor part having their combined area. These results are plotted in FIG. 8.

Figure 9:
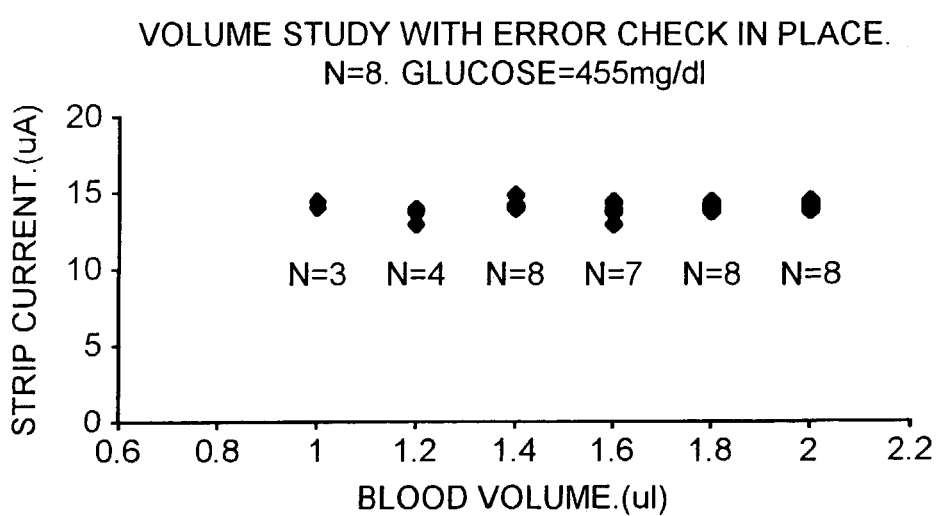
FIG. 9 is a plot similar to FIG. 8 obtained using a method in accordance with the invention.

In the second half of the test the two currents were first compared. Only if they differed by less than 10% were they then added together and put forward as valid results. Values differing by more than 10% were disregarded. The results of this second part of the test are plotted in FIG. 9.

It is immediately apparent that the second set of results is significantly more precise, i.e. they display a much lower variation. Furthermore, since in practice the two working sensor parts will only give results consistent with one another if they are both fully covered, the second set of results is also significantly more accurate than the first since it may be safely assumed that the results are only actually given when both working sensor parts are fully covered.

Thus is will-be seen that in its preferred embodiment the present invention allows the detection and rejection of those tests that have had insufficient sample applied to the test strip i.e those in which the test strip has been incorrectly used.

It will be appreciated by those skilled in the art that many variations on what has been described above are possible within the scope of the invention. For example the invention may be used to measure the level of any suitable substance in any liquid, not just glucose in blood. Furthermore, the working sensor parts need not be provided on a test strip but may be part of an integrated device. Also the difference figure of 10% used in the embodiment described above is purely exemplary and any suitable figure may be chosen.

TABLE 1

| Volume μL | Working 1: μA | Working 2: μA | % Difference | Error checked | No error check |
|---|---|---|---|---|---|
| 1 | 7.07 | 0.00 | −706800 | | 7.07 |
| 1 | 6.94 | 5.98 | −16.2175732 | | 12.92 |
| 1 | 5.53 | 0.01 | −92050 | | 5.54 |
| 1 | 6.99 | 7.09 | 1.42393909 | 14.09 | 14.09 |
| 1 | 7.34 | 7.02 | −4.59016393 | 14.35 | 14.35 |
| 1 | 7.16 | 6.79 | −5.49742078 | 13.94 | 13.94 |
| 1 | 7.01 | 3.47 | −102.13441 | | 10.48 |
| 1 | 7.07 | 5.69 | −24.2578605 | | 12.77 |
| 1.2 | 7.18 | 4.54 | −58.2286847 | | 11.72 |
| 1.2 | 7.00 | 6.78 | −3.35055351 | 13.78 | 13.78 |
| 1.2 | 7.09 | 1.79 | −297.032475 | | 8.88 |
| 1.2 | 6.31 | 0.00 | −157550 | | 6.31 |
| 1.2 | 6.78 | 6.79 | 0.11788977 | 13.56 | 13.56 |
| 1.2 | 6.95 | 6.59 | −5.4029443 | 13.53 | 13.53 |
| 1.2 | 6.62 | 6.28 | −5.36795158 | 12.89 | 12.89 |
| 1.2 | 7.23 | 3.78 | −91.2721502 | | 11.01 |
| 1.4 | 7.16 | 6.90 | −3.76811594 | 14.06 | 14.06 |
| 1.4 | 7.14 | 6.94 | −2.88184438 | 14.08 | 14.08 |
| 1.4 | 7.17 | 7.02 | −2.13675214 | 14.19 | 14.19 |
| 1.4 | 7.02 | 6.01 | −1.5918958 | 13.93 | 13.93 |
| 1.4 | 6.95 | 6.91 | −0.5788712 | 13.86 | 13.86 |
| 1.4 | 6.93 | 6.88 | −0.72674419 | 13.81 | 13.81 |
| 1.4 | 7.09 | 6.92 | −2.4566474 | 14.01 | 14.01 |
| 1.4 | 7.25 | 7.40 | 2.02702703 | 14.65 | 14.65 |
| 1.6 | 7.808 | 6.59 | −18.4825493 | | 14.40 |
| 1.6 | 6.774 | 6.589 | −2.80770982 | 13.36 | 13.36 |
| 1.6 | 6.928 | 6.904 | −0.34762457 | 13.83 | 13.83 |
| 1.6 | 6.892 | 6.453 | −6.80303735 | 13.35 | 13.35 |
| 1.6 | 7.087 | 7.314 | 3.10363686 | 14.40 | 14.40 |
| 1.6 | 7.257 | 6.947 | −4.46235785 | 14.20 | 14.20 |
| 1.6 | 6.501 | 6.306 | −3.09229305 | 12.81 | 12.81 |
| 1.6 | 6.811 | 6.755 | −0.82901554 | 13.57 | 13.57 |
| 1.8 | 7.145 | 6.536 | −9.31762546 | 13.68 | 13.68 |
| 1.8 | 7.021 | 6.612 | −6.18572293 | 13.63 | 13.63 |
| 1.8 | 6.917 | 6.828 | −1.30345636 | 13.75 | 13.75 |
| 1.8 | 6.971 | 6.78 | −2.81710914 | 13.75 | 13.75 |
| 1.8 | 7.016 | 6.941 | −1.08053595 | 13.96 | 13.96 |
| 1.8 | 6.977 | 7.179 | 2.81376236 | 14.16 | 14.16 |
| 1.8 | 6.946 | 6.794 | −2.23726828 | 13.74 | 13.74 |
| 1.8 | 7.203 | 7.183 | −0.27843519 | 14.39 | 14.39 |
| 2 | 7.145 | 6.536 | −9.31762546 | 13.68 | 13.68 |
| 2 | 7.021 | 6.621 | −6.18572293 | 13.63 | 13.63 |
| 2 | 6.917 | 6.828 | −1.30345636 | 13.75 | 13.75 |
| 2 | 6.971 | 6.78 | −2.81710914 | 13.75 | 13.75 |
| 2 | 7.016 | 6.941 | −1.08053595 | 13.96 | 13.96 |
| 2 | 6.977 | 7.179 | 2.81376236 | 14.16 | 14.16 |
| 2 | 6.946 | 6.794 | −2.23726818 | 13.74 | 13.74 |
| 2 | 7.203 | 7.183 | −0.27843519 | 14.39 | 14.39 |

The invention claimed is:

1. A method of measuring the concentration of a substance in a sample liquid comprising the steps of:
   providing a measuring device said device comprising:
      a first working sensor part for generating charge carriers in proportion to the concentration of said substance in the sample liquid;
      a second working sensor part downstream from said first working sensor part also for generating charge carriers in proportion to the concentration of said substance in the sample liquid wherein said first and second working sensor parts are arranged such that, in the absence of an error condition, the quantity of said charge carriers generated by said first working sensors part are substantially identical to the quantity of said charge carriers generated by said second working sensor part; and a reference sensor part upstream from said first and second working sensor parts which reference sensor part is a common reference for both the first and second working sensor parts, said reference sensor part and said first and second working sensor parts being arranged such that the sample liquid is constrained to flow substantially unidirectionally across said reference sensor part and said first and second working sensor parts; wherein said first and second working sensor parts and said reference sensor part are provided on a disposable test strip;

applying the sample liquid to said measuring device;

measuring an electric current at each working sensor part proportional to the concentration of said substance in the sample liquid;

comparing the electric current from each of the working sensor parts to establish a difference parameter; and giving an indication of an error if said difference parameter is greater than a predetermined threshold.

2. The method as claimed in claim 1 comprising measuring the current at each working sensor part after a predetermined time following application of the sample.

3. The method as claimed in claim 1 wherein the substance to be measured is glucose, and each of the working sensor parts generates charge carriers in proportion to the concentration of glucose in the sample liquid.

* * * * *